US012605256B2

(12) United States Patent
Rivera, Jr.

(10) Patent No.: US 12,605,256 B2
(45) Date of Patent: Apr. 21, 2026

(54) IMPLANT REMOVAL TOOL

(71) Applicant: DePuy Ireland Unlimited Company, Ringaskiddy (IE)

(72) Inventor: Jose S. Rivera, Jr., Naples, FL (US)

(73) Assignee: DEPUY IRELAND UNLIMITED COMPANY, Cork (IE)

( * ) Notice: Subject to any disclaimer, the term of this patent is extended or adjusted under 35 U.S.C. 154(b) by 0 days.

(21) Appl. No.: 18/389,795

(22) Filed: Dec. 20, 2023

(65) Prior Publication Data

US 2024/0115397 A1    Apr. 11, 2024

Related U.S. Application Data

(63) Continuation of application No. 17/515,941, filed on Nov. 1, 2021, now Pat. No. 11,890,204, which is a continuation of application No. 16/431,879, filed on Jun. 5, 2019, now Pat. No. 11,191,651.

(51) Int. Cl.
　A61F 2/46　　　　(2006.01)
　A61F 2/36　　　　(2006.01)
(52) U.S. Cl.
　CPC .......... A61F 2/4607 (2013.01); A61F 2/3662 (2013.01); A61F 2/4603 (2013.01); A61F 2002/4619 (2013.01)
(58) Field of Classification Search
　CPC ............ A61F 2002/4619; A61F 2/4607; A61F 2/4603; A61B 17/1664; A61B 17/155; A61B 17/1604; A61B 17/16; A61B 17/164; A61B 17/1668; A61B 17/1732
　See application file for complete search history.

(56) References Cited

U.S. PATENT DOCUMENTS

| | | | |
|---|---|---|---|
| 4,222,382 A | 9/1980 | Antonsson et al. |
| 4,736,738 A | 4/1988 | Lipovsek et al. |
| 4,838,853 A | 6/1989 | Parisi |
| 5,019,083 A | 5/1991 | Klapper et al. |
| 5,167,619 A | 12/1992 | Wuchinich |
| 5,257,995 A | 11/1993 | Umber et al. |

(Continued)

FOREIGN PATENT DOCUMENTS

| | | |
|---|---|---|
| GB | 2560956 A | 10/2018 |
| JP | 2013523289 A | 6/2013 |

(Continued)

OTHER PUBLICATIONS

Japanese Office Action issued Jan. 31, 2024 in corresponding Japanese Patent Application No. 2021-572565, 7 pages.

(Continued)

*Primary Examiner* — Matthew J Lawson
(74) *Attorney, Agent, or Firm* — XSENSUS LLP

(57) ABSTRACT

An implant removal tool used to remove a femoral implant from a femur bone by providing a substantially U-shaped body having a substantially rectangular-shaped opening located thereon that allows the substantially U-shaped body to be placed over a neck of a femoral implant so a sharpened front edge of the substantially U-shaped body makes direct contact with an inner surface of the stem of the femoral implant. The U-shaped body may have front side edges that extend beyond a front edge to allow the front side edges to cut anterior and posterior surface of the implant.

10 Claims, 5 Drawing Sheets

(56) References Cited

U.S. PATENT DOCUMENTS

| | | | | |
|---|---|---|---|---|
| D344,801 S | 3/1994 | Hughes et al. | | |
| 5,318,570 A | 6/1994 | Hood et al. | | |
| 5,342,366 A | 8/1994 | Whiteside et al. | | |
| 5,405,349 A * | 4/1995 | Burkinshaw | A61B 17/1675 | |
| | | | | 606/88 |
| 5,716,405 A | 2/1998 | Mittelman | | |
| 5,820,315 A * | 10/1998 | Collard | B23B 51/0426 | |
| | | | | 408/209 |
| 5,885,301 A | 3/1999 | Young | | |
| 5,961,522 A | 10/1999 | Mehdizadeh | | |
| 6,126,664 A * | 10/2000 | Troxell | A61B 17/1604 | |
| | | | | 606/87 |
| 6,187,012 B1 | 2/2001 | Masini | | |
| 6,790,211 B1 | 9/2004 | McPherson et al. | | |
| 7,744,616 B2 | 6/2010 | O'Donoghue | | |
| 7,935,118 B2 | 5/2011 | Vendrely et al. | | |
| 8,545,507 B2 | 10/2013 | Vendrely et al. | | |
| 9,603,720 B2 | 3/2017 | Kelley | | |
| 9,730,705 B2 | 8/2017 | Smith et al. | | |
| 9,867,628 B2 | 1/2018 | Macke | | |
| 9,876,628 B2 | 1/2018 | Golitschek Edler von Elbwart et al. | | |
| 10,751,070 B2 | 8/2020 | Pendleton et al. | | |
| 11,191,651 B1 | 12/2021 | Rivera, Jr. | | |
| 2002/0068941 A1 | 6/2002 | Hanson et al. | | |
| 2002/0091387 A1 | 7/2002 | Hoogland | | |
| 2003/0236525 A1 | 12/2003 | Vendrely et al. | | |
| 2004/0162619 A1 | 8/2004 | Blaylock et al. | | |
| 2005/0090829 A1 * | 4/2005 | Martz | A61B 17/1604 | |
| | | | | 606/167 |
| 2005/0251146 A1 | 11/2005 | Martz et al. | | |
| 2007/0123893 A1 | 5/2007 | O'Donoghue | | |
| 2008/0188878 A1 | 8/2008 | Young | | |
| 2010/0069909 A1 | 3/2010 | Taylor | | |
| 2010/0100097 A1 | 4/2010 | Wong | | |
| 2011/0004214 A1 | 1/2011 | Skaggs | | |
| 2011/0288555 A1 | 11/2011 | Szanto | | |
| 2012/0089147 A1 | 4/2012 | Kuczynski | | |
| 2012/0283793 A1 | 11/2012 | Burroughs, III | | |
| 2013/0226189 A1 | 8/2013 | Young | | |
| 2014/0276835 A1 | 9/2014 | Tally | | |
| 2014/0371750 A1 * | 12/2014 | Klein | A61B 17/1604 | |
| | | | | 606/79 |
| 2015/0039037 A1 | 2/2015 | Donner et al. | | |
| 2015/0196402 A1 | 7/2015 | Kim | | |
| 2016/0338751 A1 | 11/2016 | Kellar et al. | | |
| 2018/0206859 A1 * | 7/2018 | Pendleton | A61B 17/1637 | |
| 2018/0221171 A1 | 8/2018 | Termanini et al. | | |
| 2018/0280036 A1 | 10/2018 | Agunloye et al. | | |
| 2019/0314043 A1 | 10/2019 | Sekel | | |
| 2019/0336143 A1 | 11/2019 | Wright | | |
| 2020/0261247 A1 * | 8/2020 | Stchur | A61F 2/4014 | |
| 2021/0353432 A1 | 11/2021 | Rivera, Jr. | | |
| 2023/0172622 A1 | 6/2023 | Wright | | |
| 2024/0108475 A1 | 4/2024 | Rivera, Jr. | | |

FOREIGN PATENT DOCUMENTS

| | | | |
|---|---|---|---|
| JP | 2013208430 A | 10/2013 | |
| JP | 2018525121 A | 9/2018 | |
| WO | 92/22259 A2 | 12/1992 | |
| WO | 2012/006508 A2 | 1/2012 | |
| WO | 2020/247064 A1 | 12/2020 | |
| WO | 2022/140801 A2 | 6/2022 | |

OTHER PUBLICATIONS

Extended European search report issued on Jun. 15, 2023, in corresponding European patent Application No. 22740032.2, 8 pages.

Office Action issued on Dec. 30, 2022, in corresponding Chinese patent Application No. 202080054684.7 with partial English translation, 4 pages.

Chinese Office Action issued on Jun. 13, 2022, in corresponding Chinese Application No. 202080054684.7.

Extended European Search Report issued Aug. 5, 2022, in corresponding European Application No. 20817983.8.

International Search Report and Written Opinion mailed on Jun. 22, 2022, corresponding PCT/US22/13102, 11 pages.

Rivera Surgical, "Walson Extraction System", YouTube demonstration, Oct. 23, 2020, available URL: https://www.youtube.com/walch?v=CrD5vsMujiA.

Japanese Office Action issued Oct. 16, 2024 in corresponding Japanese Patent Application No. 2021-572565, 4 pages.

U.S. Notice of Allowance issued Apr. 23, 2025 in co-pending U.S. Appl. No. 17/387,805, 87 pages.

U.S. Notice of Allowance issued Apr. 25, 2025 in co pending U.S. Appl. No. 18/596,730, 95 pages.

U.S. Office Action issued Feb. 13, 2025 in co-pending U.S. Appl. No. 17/628,453, 108 pages.

Brazilian Preliminary Office Action issued Jun. 25, 2024 in corresponding Brazilian Patent Application No. BR112021024631-2, 5 pages.

International Search Report for PCT/US/20/27692 with an International filing dale of Apr. 10, 2020, and mailed on Jul. 17, 2020.

U.S. Office Action issued Mar. 28, 2023 in co-pending U.S. Appl. No. 17/515,941.

U.S. Final Office Action issued Jun. 6, 2023 in co-pending U.S. Appl. No. 17/515,941.

U.S. Office Action issued Sep. 24, 2024 in co-pending U.S. Appl. No. 18/596,730.

U.S. Notice of Allowance issued Sep. 28, 2024 in co-pending U.S. Appl. No. 17/515,941.

U.S. Office Action issued Oct. 15, 2024 in co-pending U.S. Appl. No. 17/387,805.

Korean Office Action issued Jan. 21, 2025 in corresponding Korean Patent Application No. 2022-7000296, 9 pages.

International Search Report issued Mar. 30, 2022 in corresponding International Patent Application No. PCT/US22/12238, 1 page.

Korean Notice of Allowance issued May 26, 2025 in corresponding Korean Patent Application No. 10-2022-7000296, 4 pages.

Japanese Notice of Allowance issued Jun. 3, 2025 in corresponding Japanese Patent Application No. 2021-572565, 4 pages (with machine-generated translation).

U.S. Notice of Allowance issued Jun. 13, 2025 in co-pending U.S. Appl. No. 17/628,453, 82 pages.

Australian Examination Report issued Oct. 23, 2025 in corresponding Australian Patent Application No. 2020286413, 3 pages.

U.S. Notice of Allowance issued Jul. 7, 2025 in co-pending U.S. Appl. No. 17/387,805, 82 pages.

U.S. Notice of Allowance issued Jul. 17, 2025 in co-pending U.S. Appl. No. 17/628,453, 78 pages.

U.S. Notice of Allowance issued Aug. 12, 2025 in co-pending U.S. Appl. No. 18/596,730, 95 pages.

Japanese Office Action issued Aug. 19, 2025 in corresponding Japanese Patent Application No. 2022-563463, 10 pages.

Australian Examination Report issued Jul. 14, 2025 in corresponding Australian Patent Application No. 2020286413, 4 pages.

Brazilian Office Action issued Nov. 11, 2025 in Brazilian Patent Application No. BR112021024631-2, 6 pages.

Japanese Notice of Allowance issued Nov. 25, 2025 in Japanese Patent Application No. 2022-563463, 5 pages.

Indian Office Action issued Feb. 12, 2026 in corresponding Indian Application No. 202317047243, 7 pages.

Indian Office Action issued Feb. 18, 2026 in corresponding Indian Patent Application No. 202247050290, 7 pages.

* cited by examiner

IMPLANT REMOVAL TOOL

CROSS-REFERENCE TO RELATED APPLICATIONS

This application is a continuation of U.S. patent application Ser. No. 17/515,941, filed Nov. 1, 2021, which is a continuation of U.S. patent application Ser. No. 16/431,879, filed Jun. 5, 2019 (now U.S. Pat. No. 11,191,651), each are fully incorporated herein for all purposes.

FIELD OF THE INVENTION

This invention relates to hip implant revision surgeries and more particularly, an implant removal tool designed to fit around an angled neck of a femoral implant to cut around a stem of the femoral implant with minimal bone loss.

BACKGROUND OF THE INVENTION

Total joint arthroplasty, particularly total hip replacements are being performed at an increasing rate in United States and in other developed countries. Unfortunately, many of these joint replacements fail over time and require revision surgery wherein the original implant is removed from the bone and replaced with a new implant. Moreover, due to the rapid increase in geriatric population, the number of patients requiring revisions of a failed hip arthroplasty is increasing.

The goal of such revision surgery is to remove the implant with minimum damage to the bone tissue. In most hip joint replacements, the implant is fixed to the bone with the help of an adhesive and through the eventual regrowth of bony tissue around the implant and into a porous surface of the metal implant. In a revision surgery, the removal of an existing implant is often a difficult task to accomplish without damage to the bone surrounding the implant.

This is especially true in femoral implants wherein a stem of the femoral implant is inserted into the superior end of the femur. An angled neck extends upward from the stem to mimic the natural neck of the femur bone and provide an attachment point for a head to be attached.

Ideally, a cutting tool is pressed firmly against the surface of the neck to ensure as little bone is removed as possible. However, the angled neck makes it nearly impossible to cut around an inner surface of the stem without angling the cutting tool and removing an excess amount of bone. As a new implant needs a minimum amount of bone support to be successful thus, the removal of excess bone can be very detrimental to a patient. In addition, the removal of this excess bone leads to increased surgery times, increased recovery times, failed replacement implants and, in some instances, the patient being confined to a wheel chair for the rest of his or her life.

Therefore, a need exists for an implant removal tool designed to fit around an angled neck of the femoral implant to cut around a stem of the femoral implant with minimal bone loss.

SUMMARY OF THE INVENTION

The primary object of the present invention is to provide an implant removal tool that fits around an angled neck of the femoral implant to cut around a stem of the femoral implant with minimal bone loss.

The present invention fulfills the above and other objects by providing an implant removal tool used to remove a femoral implant from a femur bone by providing a substantially U-shaped body having a substantially rectangular-shaped opening located thereon that allows the substantially U-shaped body to be placed over a neck of a femoral implant with the neck of the femoral implant extending through the substantially rectangular-shaped opening so a sharpened front edge of the substantially U-shaped body makes direct contact with an inner surface of the stem of the femoral implant. Once positioned, the U-shaped body may be pushed into the bone to cut the stem away from the bone while the sharpened front edge maintains substantial contact with the stem of the implant, thereby preventing the unnecessary loss of bone.

The U-shaped body may have front side edges that extend beyond a front edge to allow the front side edges to cut anterior and posterior surface of an implant.

The above and other objects, features and advantages of the present invention should become even more readily apparent to those skilled in the art upon a reading of the following detailed description in conjunction with the drawings wherein there is shown and described illustrative embodiments of the invention.

BRIEF DESCRIPTION OF THE DRAWINGS

In the following detailed description, reference will be made to the attached drawings in which.

DESCRIPTION OF THE PREFERRED EMBODIMENTS

Figure 1:
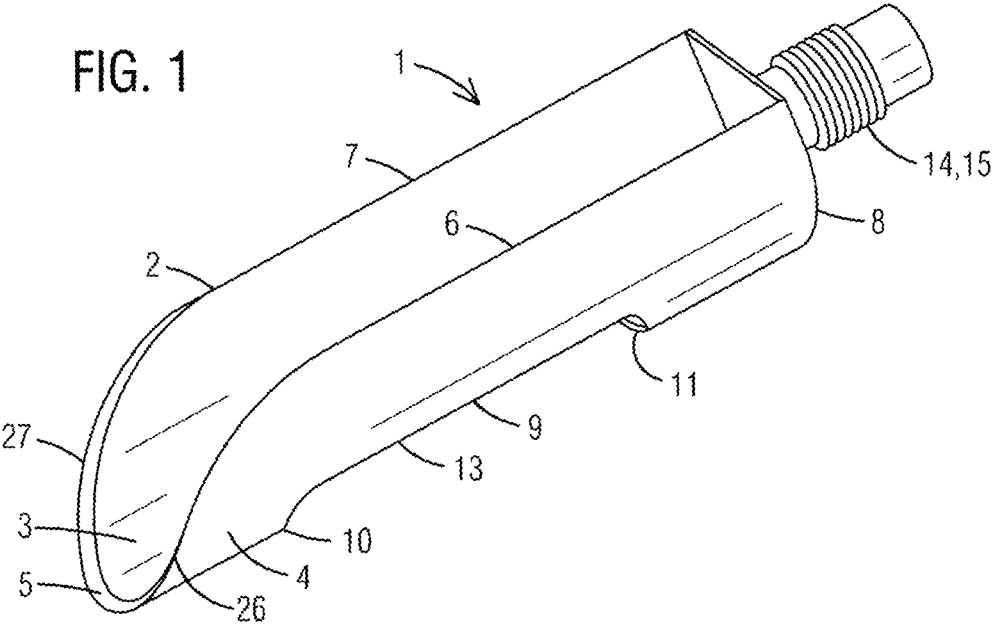
FIG. 1 is a top perspective view of an implant removal tool of the present invention.
Figure 2:
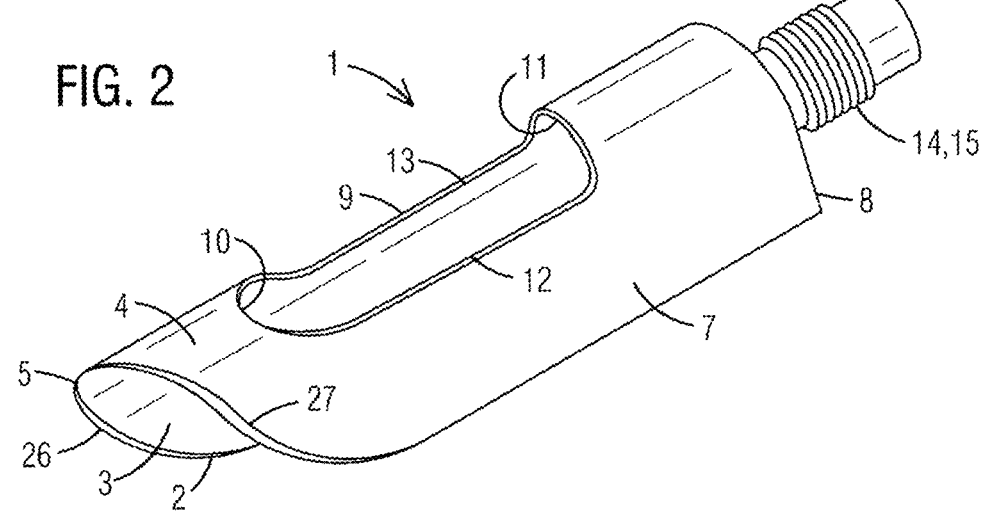
FIG. 2 is bottom perspective view of the implant removal tool of the present invention.
Figure 3:
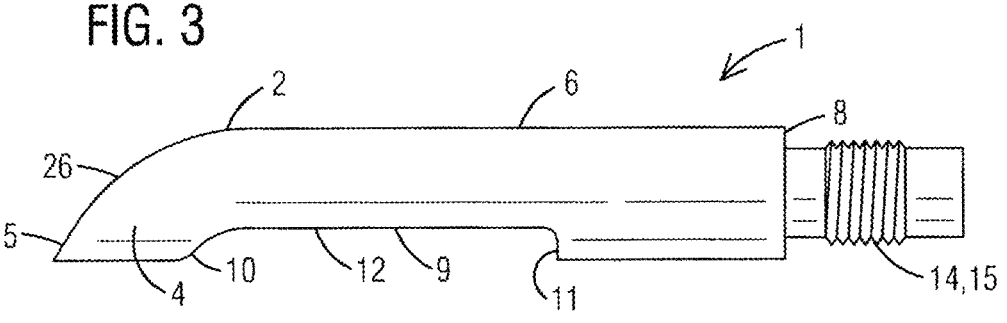
FIG. 3 is a right side view of the implant removal tool of the present invention.
Figure 4:
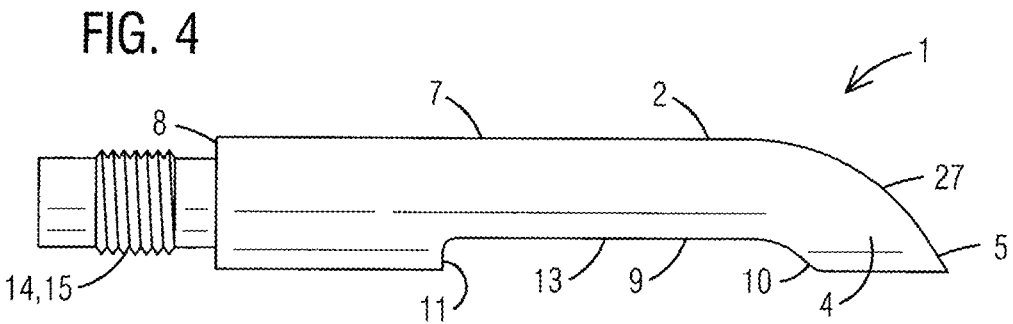
FIG. 4 is a left side view of the implant removal tool of the present invention.
Figure 5:
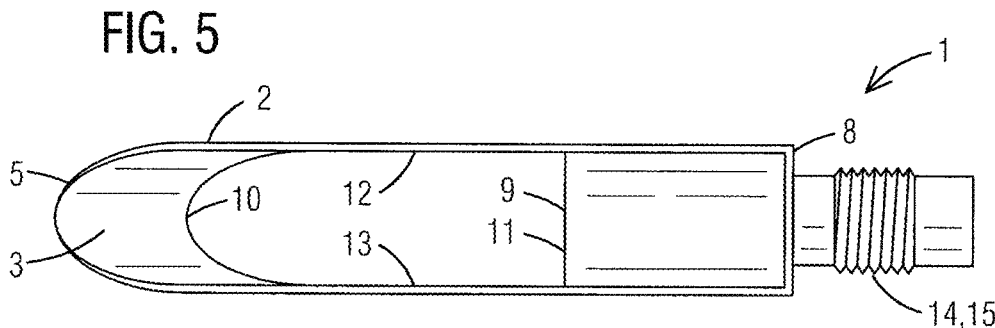
FIG. 5 is a bottom view of the implant removal tool of the present invention.
Figure 6:
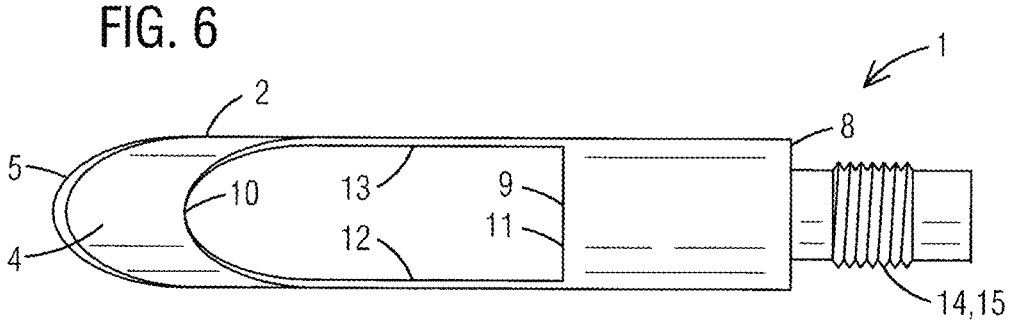
FIG. 6 is a top view of the implant removal tool of the present invention.

For purposes of describing the preferred embodiment, the terminology used in reference to the numbered accessories in the drawings is as follows:

1. implant removal tool, generally
2. U-shaped body
3. curved inner surface of U-shaped body
4. curved outer surface of U-shaped body
5. front edge of U-shaped body
6. right side edge of U-shaped body
7. left side edge of U-shaped body
8. rear surface of U-shaped body
9. rectangular-shaped opening
10. front edge of rectangular-shaped opening
11. rear edge of rectangular-shaped opening
12. right side edge of rectangular-shaped opening
13. left side edge of rectangular-shaped opening
14. attachment means
15. threaded member
16. handle
17. femoral implant
18. femur bone
19. stem
20. superior end of femur bone
21. neck
22. upper portion of stem
23. introducer
24. curved body of introducer
25. sharpened front edge of introducer
26. front right side edge of U-shaped body
27. front left side edge of U-shaped body
28. triangular-shaped point With reference to FIG. 1-6, an implant removal tool 1 of the present invention is illustrated. The implant removal tool 1 comprises a substantially U-shaped body 2 having curved inner surface 3, curved outer surface 4, front edge 5, right side edge 6, left side edge 7 and rear surface 8. The front edge 5 of the substantially U-shaped body 2 is preferably sharpened. A front right side edge 26 of the U-shaped body 2 and a front left side edge 17 of the U-shaped body 2 are also preferably sharpened.

A substantially rectangular-shaped opening 9 is located on the substantially U-shaped body 2 between the right side edge 6 and left side edge 7 thereof. The substantially rectangular-shaped opening 9 comprises a front edge 10, rear edge 11, right side edge 12 and left side edge 13. The front edge 10 of the substantially rectangular-shaped opening 9 is preferably curved to allow the front edge 10 to conform to a curved shape of a femoral implant.

Figures 8, 9:
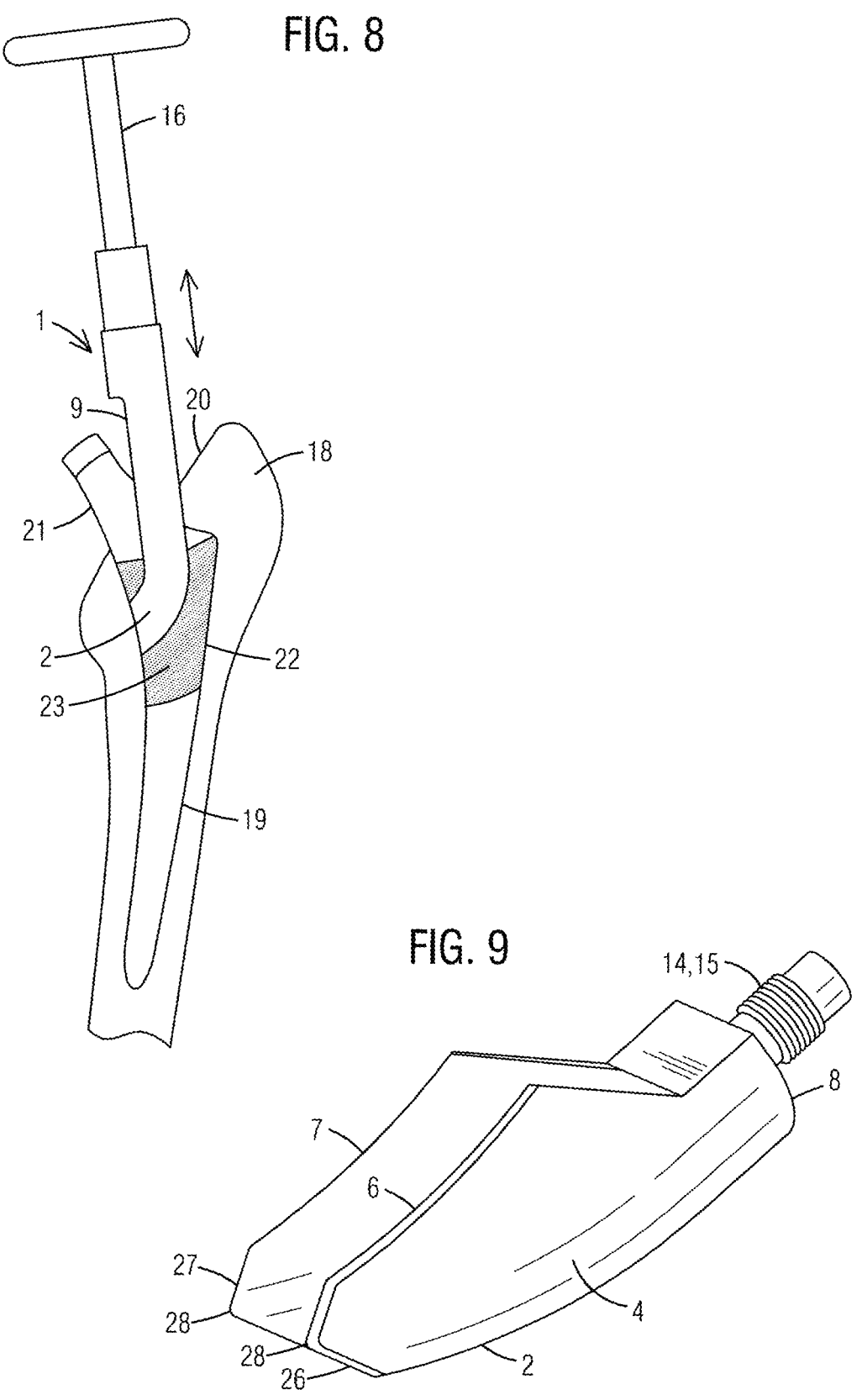
FIG. 8 is a partial cutaway view of a conventional femoral implant implanted in a femur bone and an implant removal tool of the present invention engaging the femoral implant and the femur bone.
FIG. 9 is a top perspective view of an implant removal tool of the present invention wherein front side edges extend beyond a front edge to allow the tool to cut anterior and posterior surfaces of the implant from a bone.

An attachment means 14, such as a threaded member 15, extends from the rear surface 8 of the substantially U-shaped body 2 to allow a handle 16, as illustrated in FIG. 8, to be attached to the substantially U-shaped body 2. Alternatively, a handle may be integrated into the substantially U-shaped body 2.

Figures 7, 12:
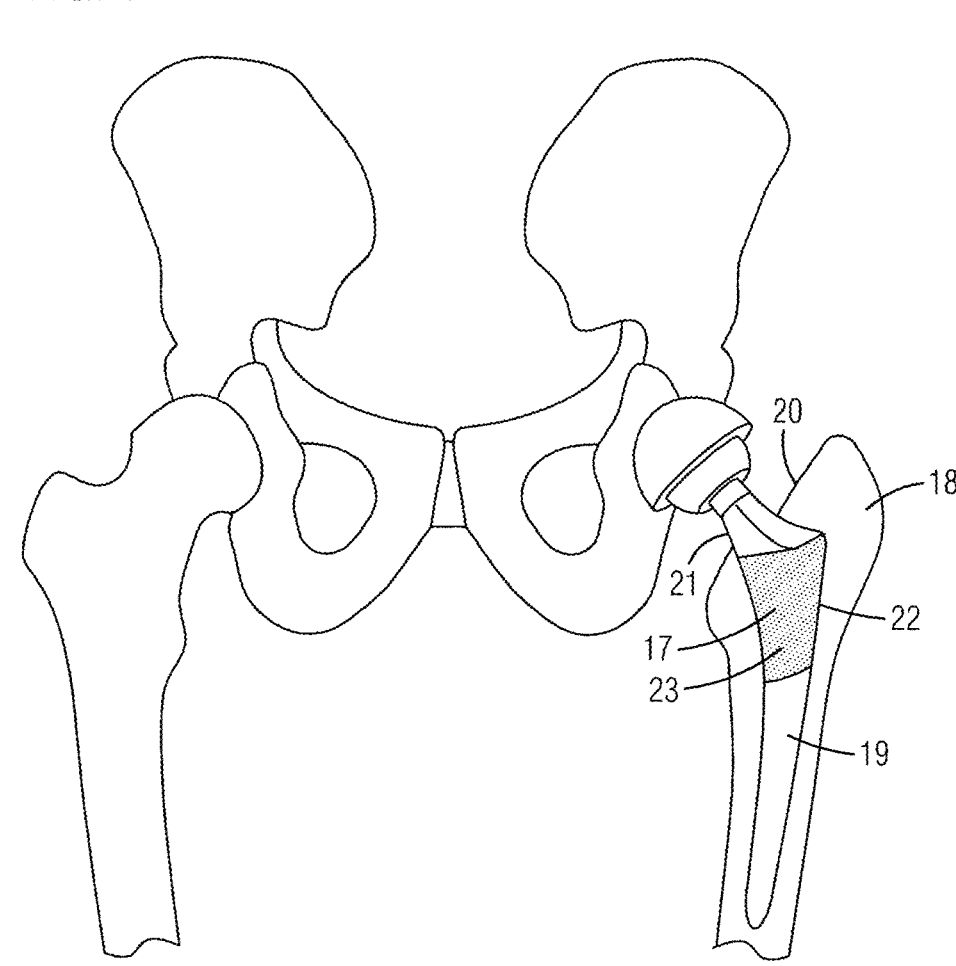
FIG. 7 is a partial cutaway view of a conventional femoral implant implanted in a femur bone.
FIG. 12 is a perspective view of an introducer of the present invention.

With reference to FIG. 7, a partial cutaway view of a conventional femoral implant 17 implanted in a femur bone 18 is illustrated. The femoral implant 17 comprises a stem 19 that is inserted into a superior end 20 of the femur bone 18. An angled neck 21 extends upward from the stem 19 at an angle and/or offset to mimic the natural neck of the femur bone 18, which has been removed from the femur bone 18. An upper portion 22 of the stem 19 is textured and/or porous to allow the femur bone 18 and/or adhesive to grip onto the stem 19 and secure it within the femur bone 18.

With reference to FIG. 8, a partial cutaway view of a conventional femoral implant 17 implanted in a femur bone 18 and an implant removal tool 1 of the present invention engaging the femoral implant 17 and the femur bone 18 is illustrated.

The substantially rectangular-shaped opening 9 allows the substantially U-shaped body 2 to be placed over a neck 21 of a femoral implant 17 with the neck 21 of the femoral implant 17 extending through the substantially rectangular-shaped opening 9 so a sharpened front edge 5 of the substantially U-shaped body 2 makes direct contact with an inner edge 23 of the stem 19 of the femoral implant 17. Once positioned, the U-shaped body 2 may be pushed into the femur bone 18 to cut the stem 19 away from the femur bone 18 while the sharpened front edge 5 maintains substantial contact with the stem 19 of the femoral implant 17, thereby preventing the unnecessary loss of the femur bone 18.

As illustrated herein, the upper portion 22 of the stem 19 and texturing located thereon only extends down the stem 19 for a predetermined distance before the stem 19 extends on. In most cases, the upper portion 22 of the stem 19 is the only portion of the femoral implant 17 that is required to be cut away from the femur bone 18. Therefore, a length of the right side edge 12 and left side edge 13 of the substantially rectangular-shaped opening 9 is preferably equal to a height of the upper portion 22 of the stem 19. This causes the rear edge 11 of the substantially rectangular-shaped opening 9 to come into contact with the angled neck 21 to prevent the sharpened front edge 5 from not extending beyond the upper portion 22 of the stem 19.

Figure 10:
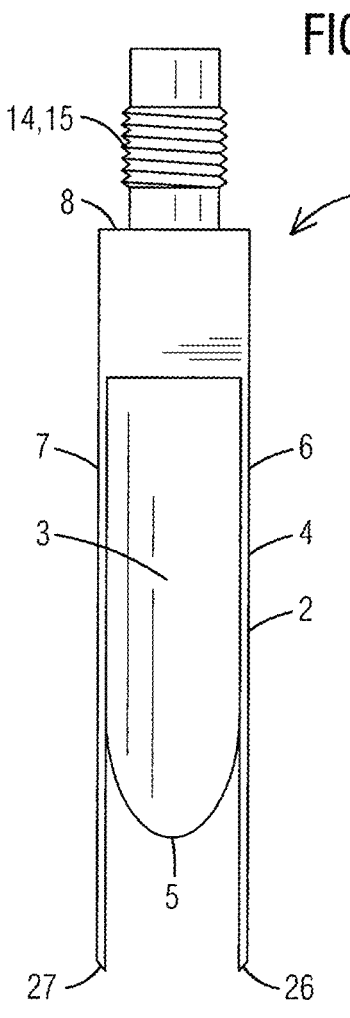
FIG. 10 is a top view of the implant removal tool of the present invention wherein front side edges extend beyond a front edge to allow the tool to cut anterior and posterior surfaces of the implant from a bone.

With reference to FIGS. 9 and 10, a top perspective view and top view, respectively, of an implant removal tool 1 of the present invention wherein front side edges extend beyond a front edge to allow the tool to cut anterior and posterior surfaces of the implant from a bone are illustrated. The implant removal tool 1 comprises a substantially U-shaped body 2 having curved inner surface 3, curved outer surface 4, front edge 5, right side edge 6, left side edge 7 and rear surface 8.

The front edge 5 of the substantially U-shaped body 2 is preferably sharpened. A front right side edge 26 of the U-shaped body 2 and a front left side edge 17 of the U-shaped body 2 are also preferably sharpened. The front right side edge 26 of the U-shaped body 2 and front left side edge 17 of the U-shaped body 2 extend beyond the front edge 5 and each form a triangular-shaped point 28.

Figure 11:
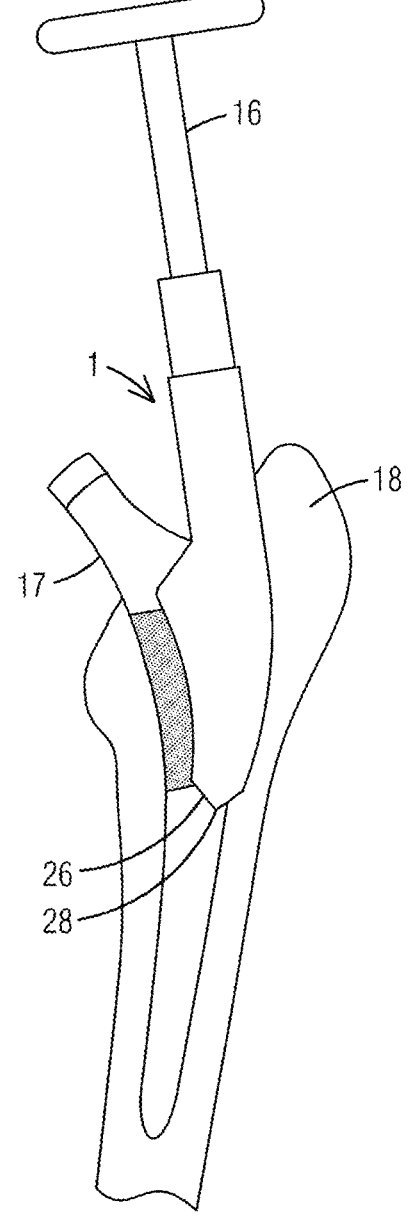
FIG. 11 is a partial cutaway view of a conventional femoral implant implanted in a femur bone and an implant removal tool of the present invention wherein front side edges extend beyond a front edge to allow the tool to cut anterior and posterior surfaces of the implant from a bone engaging the femoral implant and the femur bone.

An attachment means 14, such as a threaded member 15, extends from the rear surface 8 of the substantially U-shaped body 2 to allow a handle 16, as illustrated in FIG. 11, to be attached to the substantially U-shaped body 2. Alternatively, a handle may be integrated into the substantially U-shaped body 2.

With reference to FIG. 11, a partial cutaway view of a conventional femoral implant 17 implanted in a femur bone 18 and an implant removal tool 1 of the present invention wherein front side edges 26, 27 extend beyond a front edge 5 to allow the tool to cut anterior and posterior surfaces of the implant 17 from the femur bone 18 engaging the femoral implant 17 is illustrated.

The front edge 5 of the substantially U-shaped body 2 is preferably sharpened. A front right side edge 26 of the U-shaped body 2 and a front left side edge 17 of the U-shaped body 2 are also preferably sharpened. The front right side edge 26 of the U-shaped body 2 and front left side edge 17 of the U-shaped body 2 extend beyond the front edge 5 and each form a triangular-shaped point 28.

With reference to FIG. 12, a perspective view of an introducer 23 of the present invention is illustrated. The introducer 23 may be used to make an initial opening between the femur bone and the femoral implant. After the initial opening is made, then the sharpened front edge 5 of the of the implant removal tool 1 may be inserted into the initial opening. The introducer 23 preferably has an elongated curved body 24 and sharpened front edge 25 the elongated curved body 24 allows the introducer 23 to reach around the angled neck 21 to make an initial opening if necessary.

It is to be understood that while a preferred embodiment of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings.

What is claimed is:

1. An implant removal tool, comprising:
   a substantially U-shaped body including two side walls; and
   an opening in a curved portion of the substantially U-shaped body,
   wherein the opening forms a through-hole in the curved portion and is shaped to accommodate at least a portion of a femoral implant to pass therethrough,
   wherein the opening has a curved opening front edge,
   wherein the two side walls each have a side front edge that is connected to the front edge,
   wherein each of the side front edges has a triangular-shaped point extending beyond the front edge away from the opening.

2. The implant removal tool of claim 1, wherein the substantially U-shaped body has a front edge configured for cutting.

3. The implant removal tool of claim 2, wherein the front edge of the substantially U-shaped body is sharpened.

4. The implant removal tool of claim 1, wherein the curved opening front edge is curved to conform to a femoral implant.

5. The implant removal tool of claim 1, wherein the opening has an opening right side edge and an opening left side edge.

6. The implant removal tool of claim 5, wherein the opening right side edge and the opening left side edge have a length equal to a height of an upper portion of the femoral implant.

7. The implant removal tool of claim 1, wherein the opening has a width substantially equal to a distance between the two side walls.

8. The implant removal tool of claim 1, further comprising:
   a portion extending from a rear surface of the substantially U-shaped body, the portion being configured to attach a handle.

9. The implant removal tool of claim 1, further comprising:
   a handle integrated into the substantially U-shaped body.

10. The implant removal tool of claim 1, wherein each of the side front edges are sharpened.

\* \* \* \* \*